US005302121A

United States Patent [19]

Gagin

[11] Patent Number: 5,302,121

[45] Date of Patent: Apr. 12, 1994

[54] BALL-IN-SOCKET ORTHODONTIC BRACKET

[76] Inventor: William P. Gagin, 5122 S. 8th St., Sheboygan, Wis. 53081

[21] Appl. No.: 906,337

[22] Filed: Jun. 30, 1992

[51] Int. Cl.[5] .......... A61C 3/00

[52] U.S. Cl. .......... 433/10; 433/16

[58] Field of Search .......... 433/8, 10, 13, 15, 16, 433/17

[56] References Cited

U.S. PATENT DOCUMENTS

| | | | |
|---|---|---|---|
| 2,368,851 | 2/1945 | Laskin . | |
| 2,379,011 | 6/1945 | Laskin . | |
| 2,908,974 | 10/1959 | Stifter . | |
| 3,423,833 | 1/1969 | Pearlman . | |
| 3,721,005 | 3/1973 | Cohen . | |
| 3,946,488 | 3/1976 | Miller et al. . | |
| 4,243,387 | 1/1981 | Prins | 433/16 |
| 4,249,897 | 1/1981 | Anderson | 433/8 |
| 4,353,692 | 10/1982 | Karrakussoglu | 433/16 |
| 4,419,078 | 12/1983 | Pletcher | 433/10 |
| 4,487,581 | 12/1984 | Adler | 433/16 |
| 4,496,318 | 1/1985 | Connelly, Jr. | 433/14 |
| 4,498,867 | 2/1985 | Kesling | 433/16 |
| 4,531,911 | 7/1985 | Creekmore | 433/8 |
| 4,597,739 | 7/1986 | Rosenberg | 433/16 |
| 4,676,746 | 6/1987 | Klapper | 433/16 |
| 4,852,512 | 6/1989 | Kesling | 433/8 |
| 4,877,398 | 10/1989 | Kesling | 433/8 |
| 5,062,794 | 11/1991 | Miura | 433/10 |
| 5,095,602 | 3/1992 | Reher | 433/8 |
| 5,109,586 | 5/1992 | Jones | 29/160.6 |
| 5,125,832 | 6/1992 | Kesling | 433/8 |
| 5,154,607 | 10/1992 | Hanson | 433/8 |
| 5,160,261 | 11/1992 | Peterson | 433/8 |

OTHER PUBLICATIONS

Brochure entitled, "The Revolutionary Shoulder TM Bracket with Friction Control".

Kesling, Christopher, "The Tip-Edge Concept: Eliminating Unnecessary Anchorage Strain" *Journal of Clinical Orthodontics* 26:3 pp. 165–177 (Mar. 1992).

Schudy, George "The Dual Environment Bracket and the Low Pain Practice" May 1989.

Articles from *Clinical Impressions* 1:1 (1992).

"New Products: Ideal Face Mask from GAC" *PCSO Bulletin* Spring 1992.

Brochure regarding Nitinol XL: The New Controlling Factor.

Brochure regarding Auxiliaries: Edgewise Miscellaneous.

Weinberger, Bernard, "Historical Resume of the Evolution and Growth of Orthodontics", Chapter 2; "Treatment of Malocclusion–Mechanistic", Chapter 13.

Brochure regarding (1) The Dark Hidden Forces of Reaction; (2) A "Friendly" and Compatible Edgewise; (3) Five Practical Suggestions; (4) The Six Fundamental Fules; (5) The Three Orders of Bends.

*Orthodontic Appliances,* Chapter VI, pp. 80–85.

*Orthodontic Appliances,* "The Evolution of Fixed Appliances", pp. 88–92.

"The Use of Differential and Optimum Orthodontic Forces", Chapter VII, pp. 105–115.

"Socioeconomic, Historical and Bioplysical Considerations", Chapter 1, pp. 1–11.

"Biomechanical Principles of Orthodontic Tooth Movement", Chapter 10, pp. 488–543.

Andrews, Lawrence, "The Straight-Wire Appliance: Origin, Controversy, Commentary", *Journal of Clinical Orthodontics* X:2, pp. 99–195 (Jun. 1983).

Alexander, R. G., "The Vari-Simplex Discipline: Part 1 Concept and Appliance Design", *Journal of Clinical Orthodontics* X:2 , pp. 380–392 (Jun. 1983).

"The Use of Differential and Optimum Orthodontic Forces", Chapter 7, pp. 142–158.

*Primary Examiner*—Gene Mancene

*Assistant Examiner*—Nicholas D. Lucchesi

*Attorney, Agent, or Firm*—Haugen and Nikolai

[57] ABSTRACT

The present invention relates to a two piece fixed functional orthodontic bracket appliance to which a flexible archwire can be engaged. This two piece orthodontic bracket appliance allows for constant mobility through a full range of orthodontic tooth movement, and provides for greater innerbracket distance. It also allows free sliding of wires through its components in such a way as to reduce binding and friction. It also provides an irregular base which promotes mechanical bonding to teeth.

13 Claims, 2 Drawing Sheets 40
30
14
18
22
16
24
20
32
26
62
50
70
12
52
72
60
10
74

A
30
22
40
14
18
24
26
20
50
16
62
52
60
10

24
32
C
26
12
52
32
60
62
10

10
20
18
B
32
50
14
32
52
B
32
16
26
22
24

BALL-IN-SOCKET ORTHODONTIC BRACKET

BACKGROUND OF THE INVENTION

I. Field of the Invention

This invention relates generally to orthodontic brackets, and more particularly to a fixed functional bracket responsive to differential forces wherein an archwire can slide three dimensionally within the bracket in a low-friction arrangement.

II. Background of the Invention

Orthodontics encompasses the correction of dental irregularities and malocclusions by applying controlled precise forces to teeth. The type of orthodontic mechanism employed is most important because success in orthodontic treatment depends so much on the efficiency of the appliances. Orthodontists who have a high degree of biologic knowledge as well as a high degree of mechanical skill cannot produce the highest standards of treatment unless they employ the most efficient orthodontic mechanism. It is the purpose of this invention to provide such a mechanism. Several methods and mechanisms of orthodontic treatment are typically employed. The focus of this invention evolves from three, namely 1) functional (removable appliance) orthodontics, 2) light wire (fixed bracketed) orthodontics, and 3) edgewise (fixed bracketed) orthodontics. A major goal of a functional appliance is to relieve pressure on teeth and bone associated with oral musculature which allows for expansion and settling of teeth by nature. This happens as teeth occlude. Light wire mechanics offer differential force values. Early pioneers Storey and Smith define optimal orthodontic force value (delivered to a bracketed tooth) as the application of force to move teeth at a most favorable rate and with least tissue damage and pain. Light wire mechanics are generally associated with round wire. They generally allow freedom of three dimensional control (tip, torque, and rotation) by use of auxiliary components as teeth are guided to a predetermined round wire arch grid. Edgewise mechanics are accomplished by turning a rectangular wire on its side so that its edge can be engaged in a rectangular slot engraved into a bracket form. Tooth movement is achieved as three dimensional control (tip, torque, and rotation) is bent into the wire and is subsequently engaged in the rectangular bracket slot. All three methods have merit but lack in totality. Historically attempts have been made by idealists to fabricate appliances according to principals derived from engineering practices that will exert precise values, that is, force values that vary only slightly and within definite limits. These engineering principals cannot be translated without modification to the art of orthodontics. Certain material modifications have now become available that make this possible. Namely nickel titanium, high grade polycarbonate, and a large ceramic family. This invention takes advantage of these state of the art materials and allows a favorable environment as envisioned by Storey and Smith and other orthodontic forefathers and modern day idealists.

OBJECTS

It is a principle objective of the present invention to provide an orthodontic bracket appliance that has maximum mobility to move and react with state of the art elastic ideal arch forms, such as a nickel titanium alloy.

It is a further objective of the present invention to provide an orthodontic bracket appliance that will expedite orthodontic treatment with minimal adverse effect on teeth and the surrounding periodontal fiber using differential forces.

It is a further objective of the present invention to provide an orthodontic bracket appliance that when used with sequencing of new state of the art elastic ideal arch forms will reduce necessary gram forces applied to teeth.

It is a further objective of the present invention to provide an orthodontic bracket appliance that will reduce the friction created using sliding orthodontic mechanics principles.

It is a further objective of the present invention to provide an orthodontic bracket appliance that when used with state of the art elastic ideal arch forms will reduce pain associated with tooth movement.

It is a further objective of the present invention to provide an orthodontic bracket appliance that allows for increased inter-bracket distances thus allowing for maximum flexibility and working range of the new state of the art elastic ideal arch form.

It is a further objective of the present invention to provide an orthodontic bracket appliance that reduces the variety of parts necessary in an orthodontist's inventory.

It is a further objective of the present invention to provide an orthodontic bracket appliance that can integrate many orthodontic disciplines including removable, light wire and rectangular wire techniques through a control shape housing design and subsequent control shape selection.

It is a further objective of the present invention to provide an orthodontic bracket appliance having a smooth and rounded surface for maximum patient comfort.

It is a further objective of the present invention to provide an orthodontic bracket appliance that has flexibility to facilitate three-dimensional movement including first, second and third order control of teeth, namely tipping, torquing and rotation.

It is a further objective of the present invention to provide an orthodontic bracket appliance that has flexibility to allow the orthodontist to interchange control shapes without removing the bracket appliance from a patient's tooth.

It is a further objective of the present invention to provide an orthodontic bracket appliance having a control shape with receptacle features to accept rectangular, square or round dimensions for sequencing new state of the art elastic ideal arch forms.

It is a further objective of the present invention to provide an orthodontic bracket appliance that will reduce the number of patient appointments, adjustments and length of time for treatment.

It is a further objective of the present invention to provide an orthodontic bracket appliance that can be adapted to lingual orthodontic treatment.

It is a further objective of the present invention to provide an orthodontic bracket appliance capable of accepting rotating, uprighting and torquing auxiliaries.

SUMMARY OF THE INVENTION

The foregoing objectives are achieved by providing a ball-in-socket orthodontic bracket wherein the ball or control shape is adapted to receive an archwire which has been adapted to the dental malocclusion. The ball is free-floating within a control shape housing of the bracket and is responsive to differential forces to provide three-dimensional control of a tooth. The invention is a fixed-functional orthodontic bracket appliance adaptable to the surface of a tooth. The ball portion receives an archwire facilitating movement in a low-friction arrangement. The invention comprises a control shape housing adapted to be fastened to a tooth, wherein a wire restraining member, such as a control shape ball, is constrained and substantially encompassed by the control shape housing for receiving the archwire. The wire restraining member is adapted to receive the archwire both in low-friction engagement and in three-dimensional control.

The base member preferably includes an integrally defined socket for receiving the wire restraining member, which is preferably comprised of a ball.

In a further embodiment of the present invention, the control shape housing is made of a pliable material such that the ball can be snapped into place or selectively removable from the control shape housing. Thus, control shape balls can be selected and inserted into the socket having a variety of archwire receiving shapes such as strategically placed notches, slots or apertures. The control shape housing includes integrally formed and oppositely opposed tie-wings which extend upwardly and outwardly from the base and are designed to receive ligatures in more than one arrangement to facilitate restraining the archwire in the ball.

The control shape ball member is preferably a spherical member, however, it is recognized a frusto-shaped sphere would be suitable. The socket defined in the control shape housing preferably defines a side wall arcuately extending more than 180° for selectively constraining the spherical ball within the control shape housing. However, a pair of opposing concave surfaces would be suitable as well. The control shape housing further includes a slot defined therein extending upwardly from the base and laterally through the control shape housing to for receiving the archwire. This slot defines a second and third side wall continuous with the socket and each extending upwardly from the base and tapering outwardly from the slot such that each end of the slot is wider than a portion proximate the socket. The second and third sidewalls facilitate the archwire being moveable in three directions when received by the ball, and also determine the angulation of the archwire within the control shape housing.

The present invention is ideally adapted to treatment using differential forces and is adapted to provide first, second and third order corrections of teeth due to its three-dimensional mobility. The ball-in-socket arrangement can be custom configured with appropriately designed balls such that custom treatment on a patient's teeth is obtainable without removing the bracket from a tooth. Further, the innerbracket distance is substantial thus allowing for maximum flexibility and a working range of the new state of the art elastic ideal arch forms. The ball receives the archwire in a low friction arrangement to provide sliding orthodontic mechanics. This feature is critical to differential force techniques. Thus, the archwire is free to slide within the bracket ball socket as the teeth move due to the nickel titanium wire attempting to return to its original shape, which is determined by the clinician. Thus, the present invention provides several key arrangements and is ideally suited to be used with state of the art materials, such as nickel titanium, which one skilled in the art will recognize.

The foregoing features, objects, and advantages of the invention will become apparent to those skilled in the art from the following detailed description of the preferred embodiment, especially when considered in conjunction with the accompanying drawings, wherein like numerals refer to like elements.

DESCRIPTION OF THE PREFERRED EMBODIMENT

Figure 1:
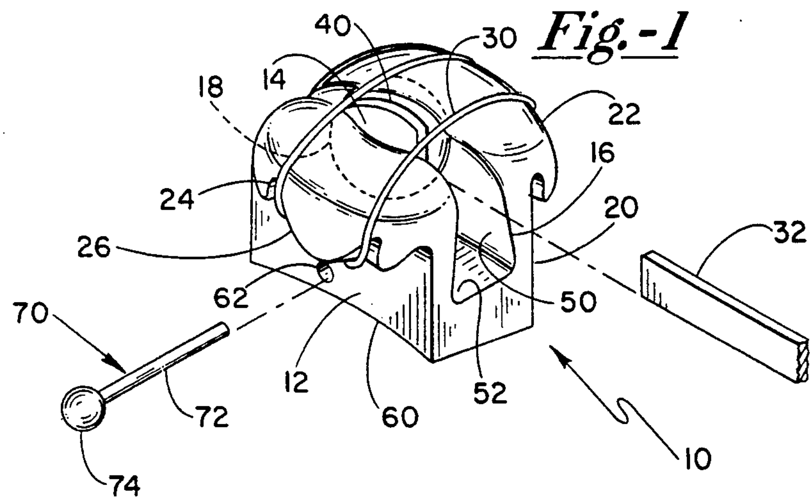
FIG. 1 illustrates a perspective view of an orthodontic appliance according to the present invention illustrating the ball-in-socket arrangement.

Referring to FIG. 1, a ball-in-socket orthodontic bracket appliance is shown and generally labeled at 10. Appliance 10 includes a first member or bracket housing 12 receiving a control shape member or ball 14. Control shape housing 12 has a rectangular shaped archwire slot 16 extending longitudinally through control shape housing 12 and opens upwardly. A spherical shaped socket 18 is integrally formed about a control portion of control shape housing 12 at an intermediate portion of slot 16 for receiving ball 14. Control shape housing 12 has a pair of stem walls 20 each extending upwardly from a base of control shape housing 12 and which is defined by both archwire slot 16 and socket 18. Stem walls 20 extend upwardly to define a pair of tie-wings 22 at an upper portion thereof and which each extend outwardly and away from slot 16. Tie-wings 22 each include a pair of integrally formed rounded notches 24 at an outer periphery thereof opposite the side proximate the slot 16. Each pair of notches 24 are arranged in a V-shape and define three lips 26 of tie-wings 22, such that an elastic ligature 30 can be adapted to each tie-wing 22 and extended over ball 14 for restraining an archwire 32 extending therethrough in ball 14. However, limitation to V-shaped notch pairs is not to be inferred as parallel pairs of notches would also be suitable. Ball 14 includes an integrally defined rectangular and upwardly facing archwire slot 40 extending radially from a midsection of ball 14. Archwire 32, which is preferably comprised of nickel titanium alloy, is slidably received within slot 40 in a fit selectably determined by the size and shape of archwire 32, wherein archwire 32 is slidable within slot 40 in a low-friction engagement. Ligature 30 shown in a first arrangement extends below each of the control lips 26 of each tie-wing 22 in notches 24 and over ball member 14 to restrain archwire 32 from movement in the upward direction.

In an optional arrangement, ligature 30 can be adapted to control shape housing 12 by placing ligature 30 completely under each of the three outer lips 24 of each tie-wing 22 and over archwire 32 to provide a locking effect such that archwire 32 is restrained from longitudinal and upward movement by ligature 30.

Figure 3:
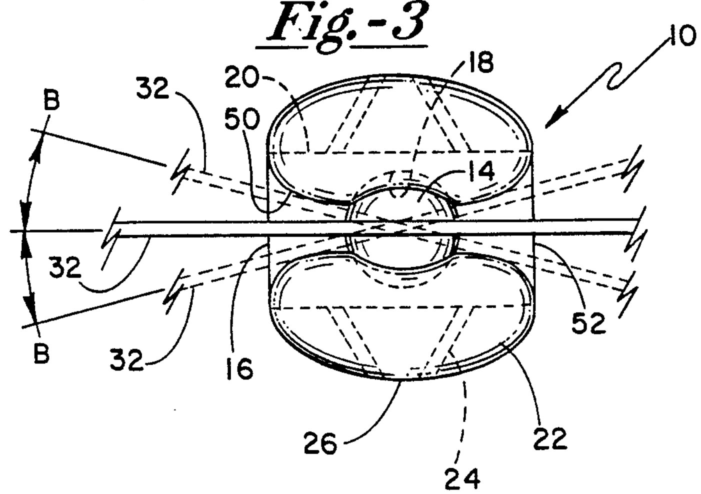
FIG. 3 illustrates a top view of the orthodontic bracket according to the present invention facilitating a second order control tip.
Figure 5:
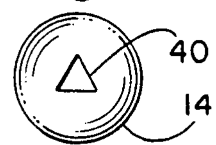
FIGS. 5-12 illustrate different embodiments of the control shape ball illustrated in FIG. 1.
Figure 9:
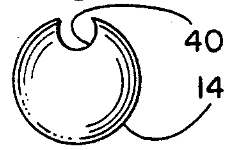
Figure 6:
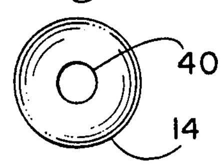
Figure 10:
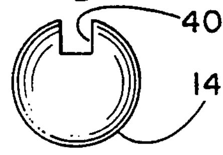
Figure 7:
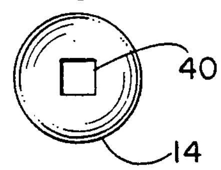
Figure 11:
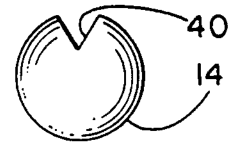
Figure 8:
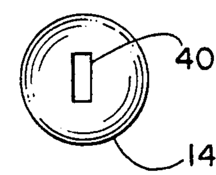
Figure 12:
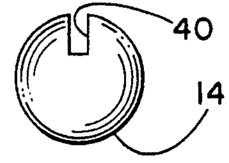

Slot 16 is defined by a pair of upwardly extending surfaces 50 of stem wall 20 which are oppositely opposed and which taper outwardly at each end such that slot 16 is wider at each end than the portion of slot 16 proximate socket 18 (see FIG. 3). Tapered surfaces 50 facilitate archwire 32 to be angled in the lateral direction with reduced interference with surfaces 50 as ball 14 rotates laterally while receiving archwire 32. An arched wall 52 of slot 16 lies in a substantially horizontal plane.

Ball 14 has a diameter only slightly less than a diameter of socket 18 such that ball 14 is constrained within control shape housing 12, yet freely rotates therein thus having three-dimensional mobility. This reduces particles, such as food, from being deposited between ball 14 and control shape housing 12. As archwire 32 moves in any or all of three-dimensions due to the characteristics of the nickel titanium alloy or other force modules, ball 14 moves therewith and translates the applied force to control shape housing 12 and ultimately the associated tooth. The width of slot 40 in ball 14 can closely conform to the width of archwire 32, or can be designed to receive archwire 32 loosely. Ball 14 is rotated, tipped, torqued, or a combination of these controls using flex generated by wire 32 as wire 32 wants to return to its pre-determined shape. New state of the art elastic arch forms will generate this flex using heat, such as provided by body temperature. These controls can also be accomplished with yet to be developed memory or magnetic concepts.

Control ball 14 is preferably comprised of a translucent polycarbonate or ceramic material for superior strength, and to provide aesthetic appeal. However, limitation to these materials is not to be inferred. Bracket housing 12 preferably is comprised of a strong plastic type material for strength, durability, easy removal, and aesthetic appeal, but could also comprise of metal material.

Control shape housing 12 has an arched bottom surface 60 conforming to the contour of the front surface of a tooth. Thus, control shape housing 12 can be securingly affixed to the labial, buccal, or lingual surface of the tooth using dental adhesives. Apparatus 10 is also adapted to be applied to a lingual tooth surface. Here, base 60 would be convex instead of concave to adapt to the innersurface of a tooth. Thus, limitation to a labial/buccal application is not to be inferred. Base 60 can also be angled to provide torque to control shape housing 12 (see FIG. 2). Control shape housing 12 can also have a variety of heights, thus, limitations to the specific ratios of the relative dimensions shown in FIG. 1 is not to be inferred.

An aperture 62 is transversely defined through the lower portion of control shape housing 12 and forms a continuous opening between respective stem walls 20 beneath base surface 52. This opening is adapted to receive a pin 70 having a shaft portion 72 and a head 74 with an outer diameter substantially equal to the diameter of aperture 62. Head portion 74 can be multishaped to accept auxiliary force modules. Aperture 62 can be designed to accept the channel stem of various rotating, uprighting, torquing or retraction springs.

Control shape housing 12 comprises a pliable material such that ball 14 may be selectively snapped in or removed from socket 18 using moderate force, such as by prying. Socket 18 is defined by an arcuate side wall integrally defined in each stem wall 20 and in base surface 52 which together arcuately extends over 180°, and preferably 200°, such that each tie-wing 22 flexes outwardly when ball 14 is removed or inserted in socket 18. This facilitates interchanging a variety of balls 14 to effect the translated force from archwire 32 to the respective tooth apparatus 10 is attached upon. However, a recess in base surface 52 is not necessary to practice the invention for the arcuate recess in each stem wall 20 are oppositely opposed to constrain ball 14 within control shape housing 12.

The top surface of ball 14 is ideally positioned slightly below a horizontal plane defined by the top surfaces of each tie-wings 22 to reduce binding of archwire 32 with ligature 30. The top surfaces of each tie-wing 22 are rounded and taper outwardly down towards each lip 26, thus providing a rounded upper surface. The combination of the rounded top surfaces of tie-wings 22 in combination with the rounded upper surface of ball 14 residing therebelow, and wherein archwire 32 is received in slot 40 and also remains below the plane defined by the top surfaces of tie-wing 22, provides an overall smooth surface which limits mouth irritation. Further, the whole apparatus 10 has a low profile for minimizing discomfort within a patient's mouth.

Figure 2:
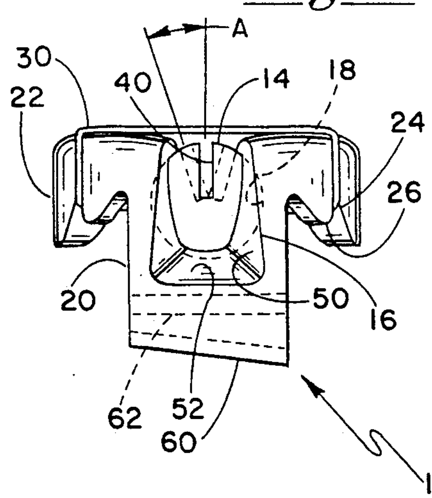
FIG. 2 illustrates an end view of the orthodontic bracket according to the present invention facilitating third order control-torque.

Referring to FIG. 2, a side view of apparatus 10 is shown. As shown, ball 14 is rotatably constrained within socket 18 and is positioned slightly below a plane defined by the upper portion of tie-wings 22. Further, ball 14 is disposed slightly above bottom surface 52 of slot 16 to help minimize friction as ball 14 freely rotates within socket 18. Notch 40 of ball 14 is shown as being rectangular, however, alternative shapes can be incorporated as shown in FIGS. 5–12. Archwire 32 can be positioned up to an angle "A" as shown to provide third order control.

Referring to FIG. 3, a top view of apparatus 10 is shown illustrating the linear alignment of slot 40 of ball 14 with slot 16 defined in control shape housing 12. As shown, each surface 50 defining slot 16 tapers outwardly at each end of slot 16 and determines the angulation of archwire 32 as ball 14 is angled in the lateral direction. As shown, archwire 32 can be positioned up to angle "B" in the lateral direction to provide second order control. FIG. 3 also illustrates the slight overlapping of socket 18 about an upper portion of ball 14 to constrain ball 14 within socket 18. Again, tie-wings 22 are pliable and can deflect outwardly when ball 14 is inserted in or removed from control shape housing 12. As shown, notches 24 form the shape of a "V" in each tie-wing 22, but could be vertical, for receiving ligature 30 about an underside and below the lips 26 of tie-wing 22, in either of the previously described arrangements.

Figure 4:
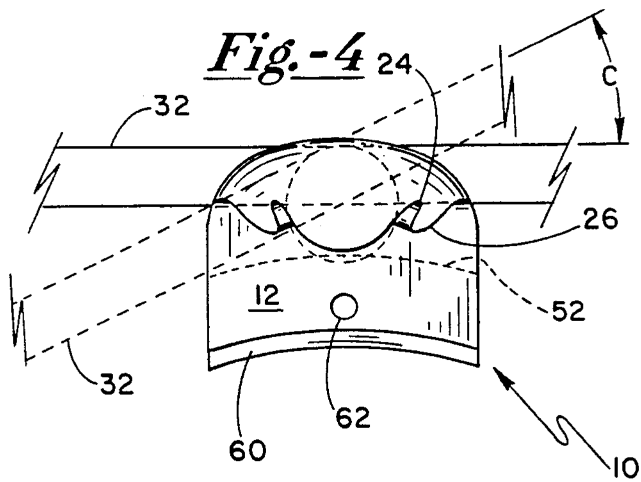
FIG. 4 illustrates a side view of the orthodontic bracket according to the present invention facilitating a first order control.

Referring to FIG. 4, a side view of apparatus 10 is shown illustrating apertures 62 extending between each stem wall 20 of control shape housing 12. FIG. 4 also illustrates the rounded design of notches 24 and lips 26 of each tie-wing 22. This figure also illustrates ball 14 being centrally located and encompassed by control shape housing 12. Archwire 32 can be positioned up to angle "C" in the vertical direction to provide first order control.

Referring to FIGS. 5–12, a variety of alternative embodiments of ball 14 are shown. In place of slot 40, apertures having a variety of shapes can also be defined extending through a midportion of ball 14 to receive archwire 32. Other uniquely shaped notches are also anticipated. Thus, limitation to the archwire receiving means to a slot 40 defined in ball 14 is not to be inferred.

Ball 14 including slot 40 receiving archwire 32 freely rotates within socket 18 and thus has a complete range of mobility. Consequently, ball 14 will rotate with archwire 32 to translate force to the associate tooth, wherein archwire 32 can be arranged in a low-friction sliding arrangement as shown in FIG. 1, to respond to differential forces. Thus, the present invention facilitates the technique of applying differential forces to urge associated teeth to be tipped, torqued, shifted vertically or laterally, or rotated about their axis thus providing a first, second or third order adjustment to the tooth. Alternately, archwire 32 can be secured to control shape housing 12 by adapting ligature 30 in the alternate arrangement, as previously described, to provide a locking feature. Thus, a more rigid rectangular archwire 32 can be received within slot 40 of ball 14 in a convenient manner to articulate or to maintain arch form.

It is also contemplated that either or both control shape housing 12 and ball 14 could include magnetic materials, such as fine particles of magnetic dust, to provide forces to the archwire 32 to affect movement thereof. Hence, limitation to non-magnetic materials is not to be inferred.

It is also contemplated that Buccal tubes affixed to rear molars for receiving the archwire 32 can be adapted to include a ball 14 without departing from the scope of the invention. The ball 14 could reside in a central portion of the tube to receive archwire 32 from an end of the tube. The ball 14 would allow freedom of movement of archwire 32 in three directions. The ball 14 could be integrally formed within the tube at the time of manufacture, or could be inserted and removed by retracting a section of the tube serving as a lid to access the ball 14. Thus, a control shape housing 12 fully enclosing a ball 14, such as a Buccal tube, is envisioned, and limitation to an "open" control shape housing with slot 16 for receiving an archwire 32 as shown in FIG. 1 is not to be inferred.

Figure 13:
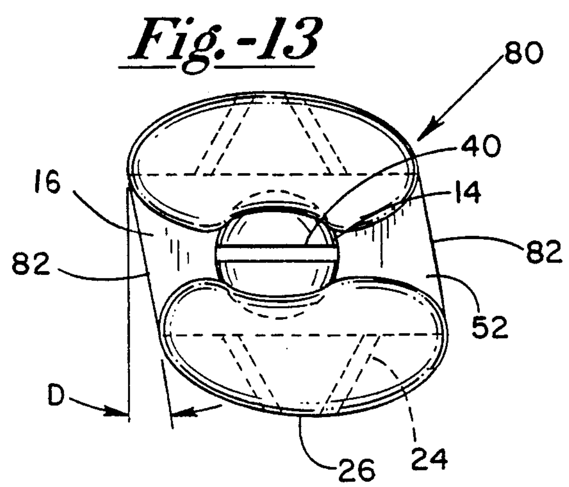
FIG. 13 illustrates an alternative embodiment of the invention.

Referring to FIG. 13, an alternative embodiment of the present invention is shown as bracket assembly 80. Assembly 80 is essentially the same as assembly 10 shown in FIG. 1 with the exception that a pair of ends 82 of control shape housing 12 are offset angle D to form a parallelogram, as shown. Slot 16 is at an acute angle with respect to ends 82 to effect torque to a respective tooth.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

I claim:

1. A fixed-functional orthodontic bracket assembly adaptable to a tooth for receiving an archwire, comprising:

(a) a control shape housing having a base portion adapted to be fastened to the tooth; and (b) wire restraining means constrained and substantially encompassed by said control shape housing for receiving said archwire, said wire restraining means having mobility in three dimensions.

2. The orthodontic bracket assembly as specified in claim 1 wherein said wire restraining means is selectively removable from said control shape housing.

3. The orthodontic bracket as specified in claim 1 wherein said control shape housing further comprises means for receiving a ligature for constraining said archwire within said wire restraining means.

4. The orthodontic bracket assembly as specified in claim 3 wherein said ligature receiving means comprises a pair of oppositely opposed tie wings each extending upwardly and outwardly from said base portion of said control shape housing.

5. The orthodontic bracket assembly as specified in claim 4 wherein each said tie wings further include a V-shaped recess for receiving said ligature.

6. The orthodontic bracket assembly as specified in claim 1 wherein said control shape housing includes an integrally formed socket.

7. The orthodontic bracket assembly as specified in claim 6 wherein said wire restraining means comprises a substantially spherical member receivable in said socket.

8. The orthodontic bracket assembly as specified in claim 7 wherein said spherical member includes an integrally formed notch for receiving said archwire.

9. The orthodontic bracket assembly as specified in claim 7 wherein said spherical member includes an aperture extending therethrough for receiving said archwire.

10. The orthodontic bracket assembly as specified in claim 7 wherein said socket defines a first sidewall in said control shape housing arcuately extending more than 180° for constraining said spherical member.

11. The orthodontic bracket assembly as specified in claim 10 wherein said first sidewall is pliable such that said spherical member may be selectively removed and replaced from said socket.

12. The orthodontic bracket assembly as specified in claim 10 wherein said control shape housing further comprises a slot defined therein extending upwardly from said base portion and laterally through said socket for receiving said archwire.

13. The orthodontic bracket assembly as specified in claim 12 wherein said slot defines a second and third sidewall each extending upwardly from said base portion and each tapering outwardly such that each end of said slot is wider than a portion proximate the socket.

* * * * *